United States Patent [19]

Fleckenstein et al.

[11] Patent Number: 4,942,266

[45] Date of Patent: Jul. 17, 1990

[54] PROCESS FOR PRODUCING FATTY ALCOHOLS AND $C_3$ DIOLS BY CATALYTIC HYDROGENATION

[75] Inventors: Theo Fleckenstein, Hilden; Gerd Goebel, Erkrath; Franz-Josef Carduck, Haan; Norbert Bremus, Langenfeld; Reinhard Eicher, Duesseldorf, all of Fed. Rep. of Germany

[73] Assignee: Henkel Kommanditgesellschaft auf Aktien, Dusseldorf-Holthausen, Fed. Rep. of Germany

[21] Appl. No.: 326,185

[22] Filed: Mar. 17, 1989

[30] Foreign Application Priority Data

Mar. 19, 1988 [DE] Fed. Rep. of Germany ....... 3809270

[51] Int. Cl.$^5$ .................... C07C 29/136; C07C 31/20; C07C 31/125
[52] U.S. Cl. ...................................... 568/864; 568/885
[58] Field of Search ................................ 568/885, 864

[56] References Cited

U.S. PATENT DOCUMENTS

| | | | |
|---|---|---|---|
| 2,109,844 | 3/1938 | Lazier | 568/885 |
| 4,804,790 | 2/1989 | Schuett | 568/885 |

FOREIGN PATENT DOCUMENTS

| | | | |
|---|---|---|---|
| 749069 | 5/1956 | United Kingdom | 568/885 |
| 975134 | 11/1964 | United Kingdom | 568/885 |

OTHER PUBLICATIONS

Ullmann Enzyklopaedie, vol. 3, p. 500 et seq. as discussed in specification.
Chemie-Technik, vol. 4, (1975) No. 12, pp. 439–441 as discussed in specification.

*Primary Examiner*—J. E. Evans
*Attorney, Agent, or Firm*—Ernest G. Szoke; Wayne C. Jaeschke; John E. Drach

[57] ABSTRACT

A process for the catalytic hydrogenation of liquid fatty acid triglycerides and the simultaneous recovery of fatty alcohols and $C_3$ diols in the presence of gaseous hydrogen and hydrogenation catalysts under pressures of from 50 to 300 bar and at temperatures in the range from 160° to 250° C., to produce fatty alcohols in at least 99% of the theoretical yield and of 1,2-propanediol in at least 80% of the theoretical yield and a maximum paraffin content of 0.5% of the theoretical yield is disclosed. The hydrogenation reaction is carried out in a tube bundle reactor operated under isothermal conditions through a cooling or heating fluid, the liquid phase being passed as co-current trickle phase with the gaseous phase over catalyst packings in the individual reactor tubes without back-mixing, and in that the load per unit volume of the reactor is selected between 0.2 and 2.5 l starting material per l reactor volume per hour and the load per unit area of each individual reactor tube between 1.5 and 25 m$^3$ starting material per m$^2$ reactor cross-section per hour and the reaction parameters of temperature and pressure are adapted in accordance with the actual catalyst activity.

11 Claims, 1 Drawing Sheet

PROCESS FOR PRODUCING FATTY ALCOHOLS AND C₃ DIOLS BY CATALYTIC HYDROGENATION

BACKGROUND OF THE INVENTION

1. Field of the Invention

This invention relates to a process for the catalytic hydrogenation of liquid fatty acid triglycerides for the simultaneous recovery of fatty alcohols and $C_3$ diols in the presence of gaseous hydrogen and hydrogenation catalysts under pressures of from 50 to 300 bar and at temperatures of from 160° to 250° C.

2. Description of the Related Art

A process of this type is known in German patent application No. DE 36 24 812. This process uses catalysts based on copper chromite with which it is possible to control the direct hydrogenation of triglycerides to fatty alcohols with high activity and selectivity under comparatively moderate reaction conditions in such a way that propane-1,2-diol is obtained as valuable secondary product and may be used for the production of alkyd or polyester resins and for many other applications.

Since these and also other hydrogenation catalysts catalyze the degradation of the valuable product, propane-1,2-diol, to secondary products and the degradation of the fatty alcohols to paraffins under hydrogenation conditions with an increase in the residence time of the reaction mixture, the hydrogenation reaction can only be stopped at the stage of the desired products by maintaining special process conditions. However, it is not known from DE No. 36 24 812 how the catalytic hydrogenation of triglycerides can be accomplished on an industrial scale.

Catalytic reactions of the type in question are often carried out in fixed-bed reactors in which the fluid phases are introduced into the reactor as trickle phase. Reactors of this type are described, for example, in Ullmanns Enzyklopädie der technischen Chemie, 4th Edition, Vol. 3, pages 500 et sec. In these reactors, the reaction takes place under adiabatic conditions, i.e. the temperature increases along the catalyst packing during the mostly exothermic reactions. However, since the selectivity of most catalysts is greatly dependent on temperature, changes in the reaction mechanism can occur in consequence of the changes in temperature in the reactor so that mostly unwanted secondary reactions take place. In addition, excessive temperatures can cause irreversible damage to the catalyst.

To limit the increase in temperature in the reactor, it is known that the gas phase may be passed in a large excess through the reactor or several reactors arranged one behind the other with intermediate cooling may be used. However, this method of temperature control is unsatisfactory for the hydrogenation of fatty acid triglycerides because the unwanted secondary reactions cannot be prevented in this way and the catalysts can suffer losses of activity through recrystallization and structural changes if certain temperatures are exceeded.

It is also known that catalytic reactions of the type in question can be carried out in an isothermally operated tube bundle reactor (Chemie-Technik, Vol. 4 (1975, No. 12, pages 439–441). In the so-called Bayer cold hydrogenation process, catalytic hydrogenations are carried out at low temperatures under substantially isothermal conditions so that the catalyst is not subjected to any variations in temperature and there is no danger of overheating. However, the reaction described in this literature reference is an extremely non-critical hydrogenation reaction, i.e. only one valuable product is targeted and the reaction product is not subsequently reacted to the same extent, if at all, so that if necessary unreacted components may be recycled; even an extended residence time under hydrogenation conditions does not harm the product.

Accordingly, the object of the present invention is to provide a process for the direct catalytic hydrogenation of triglycerides to fatty alcohols and propanediol under industrial conditions with yields of propanediol of more than 80% of the theoretical and with a content of paraffins of no more than 0.5% of the theoretical.

DESCRIPTION OF THE INVENTION

Figure 1:
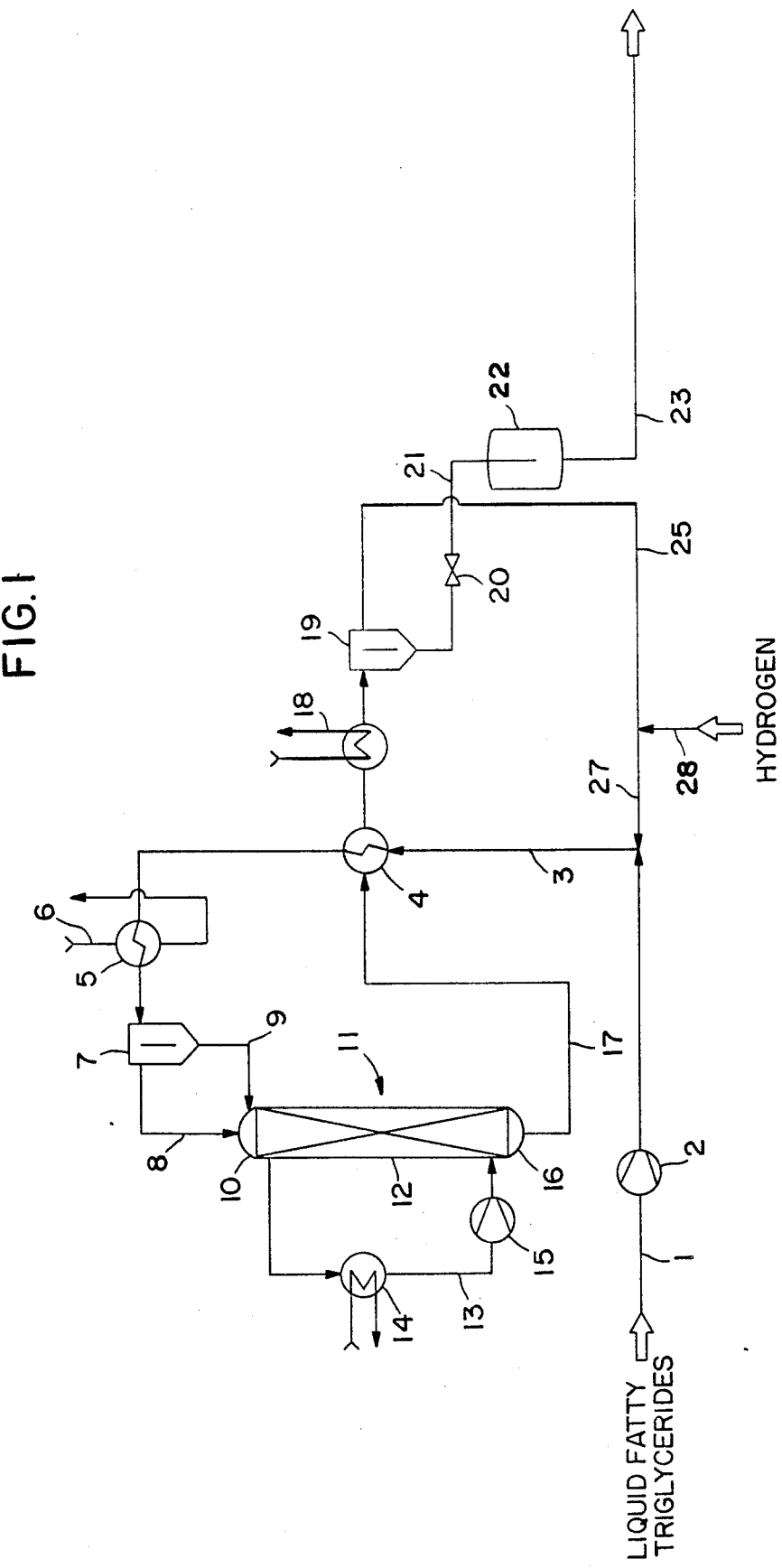
FIG. 1 illustrates a preferred arrangement for the continuous catalytic hydrogenation of liquid fatty acid triglycerides.

According to the invention, this object is achieved by a process of the type mentioned at the beginning in that the hydrogenation reaction is carried out in a tube bundle reactor operated under isothermal conditions through a cooling or heating fluid, the liquid phase being passed as co-current trickle phase with the gaseous phase over catalyst packings in the individual reactor tubes without back-mixing, and in that the reaction mixture formed is adjusted to a yield of fatty alcohols of at least 99% of the theoretical and of propane-1,2-diol of at least 80% of the theoretical and to a paraffin content of at most 0.5% of the theoretical by selecting the load per unit volume of the reactor between 0.2 and 2.5 l starting material per 1 reactor volume per hour and the load per unit area of each individual reactor tube between 1.5 and 24 m³ starting material per m² reactor cross-section per hour and adapting the reaction parameters of temperature and pressure in accordance with the actual catalyst activity.

It has surprisingly been found that, by carrying out the process in this way, the hydrogenation reaction can be controlled in such a way that the reaction can be stopped at the stage of the desired reaction products so that a yield of propane-1,2-diol of at least 80% of the theoretical and a paraffin content of at most 0.5% of the theoretical are obtained. The reaction can be controlled in this way by passing the fluid phases through the catalyst packings in the individual reactor tubes for a defined residence time without back-mixing. The reaction parameters of temperature and pressure are coordinated with one another in accordance with the particular activity of the catalyst until the desired product yields are obtained. The isothermal temperature profile in the tube bundle reactor ensures that only the desired reaction mechanisms come into play.

In one preferred embodiment of the invention, the reaction mixture is adjusted to a yield of propane-1,2-diol of greater than 80%, preferably greater than 90% and more preferably greater than 95% of the theoretical by adaptation of the reaction parameters temperature and pressure. To this end, the reaction parameters of temperature and pressure are coordinated with one another until the desired product yields are obtained.

One embodiment of the invention is characterized in that, to avoid back-mixing, the internal diameter of the individual reactor tubes is selected between 25 and 200 mm, preferably between 30 and 100 mm and more preferably between 40 and 70 mm and the mobile phases are passed through the catalyst packing in plug flow characteristic. These dimensions of the individual reactor tubes ensure that the fluid phases flow through the catalyst packing in plug flow characteristic so that there can be no back-mixing which could lead to uncontrolled reactions. This provides for precise conduct of the reaction to obtain the desired reaction product.

In one particularly practical embodiment, the load per unit volume is adjusted to values between 0.3 and 2.0 l starting material per 1 reactor volume per hour. At the same time, the load per unit area of each individual reactor tube is advantageously adjusted to a value between 1.5 and 15 $m^3$ starting material per $m^2$ reactor cross-section per hour. These special process conditions provide for particularly precise conduct of the reaction.

In another preferred embodiment of the invention, the maximum temperature increase in the reaction zone is adjusted to at most 5° C. by internal cooling through an excess of hydrogen and/or by external cooling through the cooling fluid. This very precise control of temperature ensures that there are no unwanted secondary reactions and that the catalyst does not suffer any heat damage.

In other embodiments of the invention, the process is carried out at temperatures of from 180° to 250° C. and under pressures of from 150 to 280 bar. These process parameters have proved to be particularly favorable.

Particularly good hydrogenation results are obtained if particulate or shaped catalysts based on copper chromite, of the type described in copending U.S. patent application Ser. No. 07/074,814, filed July 7, 1987, now abandoned, the entire contents of which are hereby incorporated be reference, are used as the catalysts.

Finally, in another embodiment of the invention, liquid phase is uniformly admitted to the individual reactor tubes through a distributor with an accuracy of 5%. This ensures that a uniform reaction takes place in all the reaction tubes so that a uniform reaction product is obtained.

The invention is described by way of example in the following with reference to the accompanying drawing which is a simplified flow chart of a plant for the hydrogenation of triglycerides.

Referring to FIG. 1, a plant for the direct hydrogenation of fatty acid triglycerides comprises a pipe 1 with a pump 2 by which liquid fatty acid triglycerides are delivered to the plant. The pipe 1 opens into a pipe 3 which leads via a first heat exchanger 4 and a second heat exchanger 5, which is heated by a heating fluid, for example steam under high pressure, through a pipe 6, into a gas-liquid separator 7. A gas pipe 8 and a liquid pipe 9 lead from the separator 7 into the head region 10 of a tube bundle reactor 11.

The tube bundle reactor 11 shown in simplified form comprises in the reaction zone 12 a plurality of parallel, individual reactor tubes filled with catalyst packings, for example based on copper chromite. The individual tubes are cooled in countercurrent through a coolant circuit 13. A heat exchanger 14 for cooling the cooling fluid and a pump 15 are arranged in the coolant circuit 13.

A product pipe 17 leads out from the foot 16 of the tube bundle reactor 11, passing first through the heat exchanger 4 and then through another heat exchanger 18. The pipe 17 opens into a gas-liquid separator 19. The liquid reaction products, particularly fatty alcohols and propane-1,2-diol, are run off from the separator 19 through a pipe 21 with a constriction 20 into a storage container 22. The product can be removed through a pipe 23.

The gas phase issuing from the separator 19, which consists essentially of hydrogen, is removed through a pipe 25. The pipe 25 is guided into a pipe 27 into which a feed pipe 28 for fresh hydrogen opens at the same time. After the opening of the pipe 28, the pipe 27 is guided into the pipe 3.

The process takes place as follows:

Liquid fatty acid triglycerides and gaseous hydrogen are combined through the pipes 1 and 28 or 27 in the pipe 3 and heated to a temperature above about 160° C. in the heat exchangers 4 and 5. The two phases are then separated from one another in the separator 7 and introduced into the tube bundle reactor 11 through the pipes 8 and 9 at the head 10 of the reactor 11. The liquid phase is uniformly distributed among the individual tubes of the tube bundle reactor 11 through a distributor (although this is not shown in the drawing) while the gaseous hydrogen is automatically divided substantially equally among the individual tubes without a special distributor.

The liquid phase flows as trickle phase in co-current with the gas phase through the catalyst packings in the individual tubes. By virtue of the geometric dimensions of the individual reactor tubes and the exact loads per unit volume and unit area of the individual tubes, a plug flow characteristic is established in the catalyst tubes, so that no back-mixing can occur. In addition, precise conduct of the reaction is guaranteed by the exact control of temperature through the cooling circuit 13 or through an excess of hydrogen. The reaction parameters of pressure and temperature are adjusted in accordance with the actual activity of the catalyst and the flow conditions established in the reactor in such a way that the hydrogenation product has the required high yield of fatty alcohols and propane-1,2-diol and also a low paraffin content.

The reaction product issues from the individual tubes at the foot 16 of the reactor 11 so that it can no longer come into contact with the catalyst, thus preventing unwanted secondary reactions which could adversely affect the desired product composition. The reaction product and excess oxygen are then cooled through the pipe 17 in the heat exchanger 4, by which the starting product freshly introduced into the plant is simultaneously heated, and also in the heat exchanger 18 and are then delivered to the gas-liquid separator 19. The liquid reaction product comprising fatty alcohols and propane-1,2-diol is fed through the pipe 21 to the storage container 22 from which it can be removed through the pipe 23.

The gas phase separated in the separator 19, which essentially contains hydrogen, is removed through the pipe 25, mixed with fresh hydrogen from the pipe 28 and recycled through the pipes 27 and 3 to the tube bundle reactor 11.

To obtain the desired hydrogenation product, which is intended to show a yield of fatty alcohols of at least 99% of the theoretical, a yield of propane-1,2-diol of at least 80% of the theoretical and a maximum paraffin content of 0.5% of the theoretical, the reaction parameters of pressure and temperature are adapted to the catalyst activities which change with time.

The invention is not of course confined to the example of embodiment shown in the drawing. Other embodiments of the invention are possible without departing from the basic concept. Thus, the isothermal reaction conditions in the reactor may be established simply by cooling without an excess of hydrogen, etc.

What is claimed is:

1. A process for producing fatty alcohols and $C_3$ diols by the catalytic hydrogenation of fatty triglycerides comprising the steps of:
    (1) providing a feed stream comprising gaseous hydrogen and liquid fatty acid triglyceride;
    (2) passing said feed stream through a tube bundle reactor having a hydrogenation catalyst therein at a volume load rate of about 0.2 to about 2.5 liters of said feed stream per liter of reactor volume per hour and at a area load rate of about 1.5 to about 24 $m^3$ feed stream per $m^2$ of reactor cross-section per hour to produce at least an 80% yield of 1,2-propanediol and at least a 99% yield of fatty alcohols and less than a 0.5% yield of paraffin.

2. The process of claim 1 wherein the diameter of the individual tubes in said tube bundle reactor is from about 25 mm to about 200 mm.

3. The process of claim 2 wherein the diameter of the individual tubes in said tube bundle reactor is from about 30 mm to about 100 mm.

4. The process of claim 3 wherein the diameter of the individual tubes in said tube bundle reactor is from about 40 mm to about 70 mm.

5. The process of claim 1 wherein said volume load rate is from about 0.3 to about 2.0 liters of feed stream per liter of reactor volume per hour.

6. The process of claim 1 wherein said area load rate is from about 1.5 to about $15M^3$ of feed stream per $m^2$ of reactor cross-section per hour.

7. The process of claim 1 wherein said process is carried out isothermally.

8. The process of claim 1 wherein said process is carried out in the temperature range of from about 180° C. to about 250° C.

9. The process of claim 1 wherein said process is carried out in the pressure range of from about 150 bar to about 280 bar.

10. The process of claim 1 wherein the temperature at which said process is carried out increases by less than 5° C.

11. The process of claim 1 wherein said hydrogenation catalyst is copper chromite-based and in the form of granulates or extrudates.

* * * * *